United States Patent [19]

Farng et al.

[11] Patent Number: 4,919,830
[45] Date of Patent: Apr. 24, 1990

[54] DITHIOCARBAMATE-DERIVED PHOSPHATES AS ANTIOXIDANT/ANTIWEAR MULTIFUNCTIONAL ADDITIVES

[75] Inventors: Liehpao O. Farng, Lawrenceville; Andrew G. Horodysky, Cherry Hill, both of N.J.

[73] Assignee: Mobil Oil Corporation, New York, N.Y.

[21] Appl. No.: 292,064

[22] Filed: Dec. 30, 1988

[51] Int. Cl.$^5$ .......................................... C10M 137/04
[52] U.S. Cl. .............................. 252/327 E; 558/170
[58] Field of Search .................... 252/32.7 E, 32.7 R, 252/46.7, 47.5

[56] References Cited

U.S. PATENT DOCUMENTS

| | | | |
|---|---|---|---|
| 3,462,368 | 8/1969 | Wollensak et al. | 252/46.7 |
| 3,840,463 | 10/1974 | Froeschmann et al. | 252/32.7 E |
| 4,104,181 | 8/1978 | Landis et al. | 252/46.7 |
| 4,511,481 | 4/1985 | Shim | 252/32.5 |
| 4,534,794 | 8/1985 | Walter et al. | 106/14.05 |
| 4,692,256 | 9/1987 | Umemura et al. | 252/32.7 E |
| 4,758,614 | 7/1988 | Pastor et al. | 524/101 |

Primary Examiner—William R. Dixon, Jr.
Assistant Examiner—Rhonda R. Brown
Attorney, Agent, or Firm—Alexander J. McKillop; Charles J. Speciale; Howard M. Flournoy

[57] ABSTRACT

Dihydrocarbyl dithiocarbamate-derived organic phosphates have been found to be effective antioxidant/antiwear multifunctional additives for various lubricant media.

33 Claims, No Drawings

DITHIOCARBAMATE-DERIVED PHOSPHATES AS ANTIOXIDANT/ANTIWEAR MULTIFUNCTIONAL ADDITIVES

BACKGROUND OF THE INVENTION

The use of metal dithiocarbamates, such as zinc, nickel, or lead dialkyl dithiocarbamates, are known as effective antioxidants and antiozonants for many rubbers and polymers in various kinds of applications, such as styrene butadiene rubber.

The use of non-metallic (ashless) dithiocarbamates, such as 4,4'-methylene bis(dibutyl dithiocarbamate), has been well known for antioxidant and extreme pressure properties in lubricant applications.

The use of organic phosphates, such as tricresyl phosphate and trixylyl phosphate, has been widely reported as having beneficial extreme pressure, fire resistance, and thermal stabilizing properties.

It has now been found that the use of dithiocarbamate-derived organic phosphates provides exceptional antioxidant and antiwear/EP activity with potential flame retarding, and high temperature stabilizing properties.

SUMMARY OF THE INVENTION

In accordance with the present invention, there are provided lubricant compositions comprising a lubricant and an antioxidant/antiwear amount of a product of reaction comprising a dialkyl dithiocarbamate-derived organic phosphate. Generally speaking these additive products are made by reacting an alkali-metal hydroxide with a secondary dialkylamine and carbon disulfide in an aqueous/organic media or similarly tialkyl ammonium salts of dithiocarbamates can be made by reacting trialkylamine, dialkylamine and carbon disulfide in non-aqueous media. The products of these reactions are then further reacted with a suitable organic phosphate, for example, tris(2-chloroethyl) phosphate. Accordingly, the invention is also directed to reaction products and to lubricant compositions containing them.

The use of additive concentrations of these dithiocarbamate-derived phosphates in premium quality automotive and industrial lubricants significantly enhance the stability, reduce wear and extend service life. The novel additive products described herein are useful at low concentrations and do not contain any potentially undesirable metals or cause corrosivity problems. They can be made readily commercially using economically favorable processes, implementing known technology and existing equipment.

DETAILED DESCRIPTION OF THE INVENTION

As noted hereinabove lubricant compositions containing small additive concentrations of N,N-dihydrocarbyl dithiocarbamate derived phosphates, or more preferably N,N-dialkyl dithiocarbamate-derived phosphates possess excellent antioxidant properties coupled with very good antiwear and extreme pressure load carrying activities. Both the dithiocarbamate moiety and the phosphate moiety are believed to provide the basis for the synergistic antiwear activity. The dithiocarbamate group is also believed to contribute significant antioxidant property to these novel additives.

All of these beneficial properties are believed to be enhanced as a result of this novel internal synergism. This unique internal synergism concept is believed to be applicable to similar structures containing dithiocarbamate groups, and phosphate groups within the same molecule. The products of this patent application show good stability and compatibility when used in the presence of other commonly used additives in lubricant compositions.

Generally speaking, the products of this invention are prepared as described below.

Sodium dihydrocarbyl, or more preferably dialkyl dithiocarbamates can be synthesized by reacting equal molar amounts of sodium (alkali metal) hydroxide, or alternatively oxide or hydroxide, a secondary dihydrocarbyl amine, and carbon disulfide in aqueous media or an organic solution, depending on conditions (Equation 1).

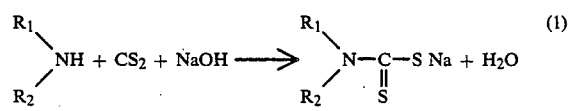

Similarly, trihydrocarbylammonium salts such as triethylammonium salts of dithiocarbamates can be made by reacting a trihydrocarbylamine such as triethylamine and carbon disulfide in an non-aqueous media (Equation 2).

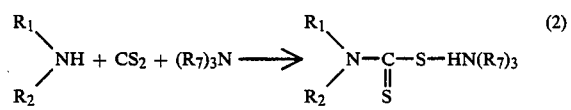

Tris(2-chloroethyl) phosphate (made by the reaction of ethylene oxide and phosphorus oxychloride and commercially avialable) was reacted with either sodium dialkyl dithiocarbamates or tiethyl ammonium salts of dialkyl dithiocarbamates to form N,N-dialkyl dithiocarbamate-derived organic phosphates as generally described in Equation 3 below.

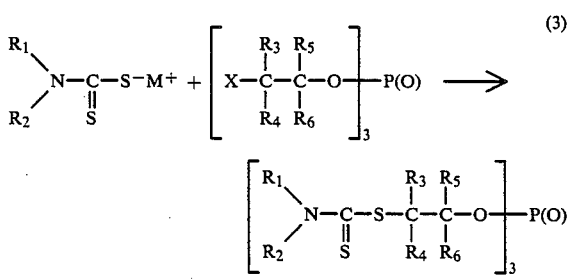

$R_1$ and $R_2$ are independently hydrogen, or $C_1$ to about $C_{60}$ hydrocarbyl, $R_3$, $R_4$, $R_5$ and $R_6$ are independently hydrogen or $C_1$ to aobut $C_{30}$ hydrocarbyl, and can optionally contain sulfur, nitrogen or oxygen.

$M^+$ represents the cationic moiety of a dithiocarbamate salt, such as an alkali metal ion e.g. a sodium ion ($Na^+$) potassium ($K^+$) ion or lithium ion ($Li^+$) or trihydrocarbyl/trialkylammonium ion $[(R_1)_3N^+H]$ such as triethylammonium $(C_2H_5)_3N^+H$, or trimethyl (propyl or butyl) ammonium ion or other suitable cations which include ions such as calcium ion ($Ca^{2+}$) where $R_7$ is $C_1$ to about $C_{30}$ hydrocarbyl or $C_1$ to about $C_{12}$ alkyl, preferably ethyl and can optionally contain sulfur, nitrogen, and/or oxygen.

Other organic phosphates with the general structure below are also available for these types of reactions.

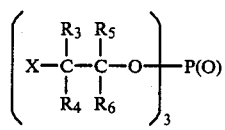

Where X is a halide (Cl, Br, I), and $R_3$, $R_4$, $R_5$ and $R_6$ are as defined above and can optionally also contain sulfur, nitrogen or oxygen.

An excess of one reagent or another can be used. However, the most promising stoichiometry is three moles of the dithiocarbamate salt to one mole of halophosphate (halo includes chloro or bromo, preferably chloro).

The reaction conditions are based primarily on the particular reactants. Usually, however, the temperature may vary from about $-50°$ C. to about $250°$ C., the pressure is generally ambient but slightly higher pressures may be used if desired and the time of reaction may vary from one to about 12 hours or more depending on the specific reactants. The molar ratio of the reactants, dithiocarbamate reactant to organic phosphate, may vary from 0.01:1 to 100:1. Other suitable reactants within the skill of the art may be utilized in the process, however, generally speaking they will conform to the structure disclosed in the above equations which describe making the novel products of the invention.

The compounds disclosed herein are used with lubricating oils to the extent to from about 0.1% to about 10% by weight of the total composition. Other additives, such as detergents, antioxidants, antiwear agents, viscosity index improvers, pour depressants, dispersants, and the like may be present. These can include but are not limited to phenates, sulfonates, succinimides, metallic zinc or ashless dithiophosphorothionyl disulfides, phosphites, sulfides, polymers, calcium and magnesium salts and the like. For example, other corrosion inhibitors, extreme pressure agents, viscosity index improvers, coantioxidants, antiwear agents and the like can be used. These materials do not detract from the value of the compositions of the invention; rather the materials serve to impart their customary properties to the particular compositions in which they are incorporated.

An important feature of the invention is the ability of the additive to improve the resistance to oxidation of oleaginous materials such as lubricating oils, either a mineral oil or a synthetic oil, or mixtures thereof, or a grease in which any of the aforementioned oils are employed as a vehicle.

In general, mineral oils, both paraffinic, naphthenic and mixtures thereof, employed as a lubricating oil or as the grease vehicle, may be of any suitable lubricating viscosity range, as for example, for about 45 SSR at 100° F. to about 6000 SSU at 100° F., and preferably from about 50 to about 250 SSR at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be including in the grease formulation.

A wide variety of materials may be employed as thickening or gelling agents. These may include any of the conventional metal salts or soaps, including calcium or lithium soaps which include calcium or lithium stearates or calcium or lithium hydroxystearates. These are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners are employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

If synthetic oils are preferred as lubricants, either per se or as a grease vehicle, various synthetic oils may be successfully utilized. Typical synthetic vehicles include polyisobutylenes, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenols, siloxanes and silicones (polysiloxanes) and alkyl-substituted diphenyl ethers typified by a butyl-substituted bis(p-phenoxy phenyl)ether, phenoxy phenylethers.

Having discussed the invention in broad and general terms, the following exemplary material illustrates it. It is to be understood that the examples are merely illustrative and are not intended to limit the scope of the invention.

EXAMPLES

Example 1

Preparation of Triethylammonium Salt of N,N-Dicoco Dithiocarbamate

Approximately 385.0 grams of dicocamine (1.0 mole), 600 milliliters toluene, and 101.3 grams of triethylamine (1.0 mole), were mixed together in a three-liter, four-neck reactor equipped with a thermometer, a Dean-Stark trap with condenser, an agitator, and a dropping funnel. Slowly, 79.6 grams of carbon disulfide (1.05 mole) was added dropwise on the stirred reactants over a course of one hour through the dropping funnel. The reaction exotherm was controlled by using ice-water for cooling and the reaction temperature was maintained below 40° C. At the end of the addition, the mixture was further stirred for one additional hour. The toluene solution of diethiocarbamate salt weighed 997 grams.

Example 2

Preparation of Sodium N,N-Di-2-Ethylhexyl Dithiocarbamate

Approximately 484 grams of di-2-ethylhexylamine (2.0 moles), 500 milliliters toluene, and 160 grams of sodium hydroxide solution (50% w/w, 2.0 moles) were charged in a two-liter, four-neck flask. Slowly, 160 grams of carbon disulfude (2.105 moles) are added dropwise through a dropping funnel to the agitated reactants over a two-hour period. The resulting exotherm was controlled with an ice-water bath to keep the reaction temperature below 30° C. At the end of the addition, the reaction mixture was gradually heated from 10° C. to 100° C., and water was azeotropically removed from the Dean-Stark trap and condenser. Approximately 97 milliliters of water were collected. It was further diluted with more toluene to make up a total of 1208 grams toluene solution of sodium dithiocarbamate.

Example 3

Reaction Product of N,N-Dicoco Dithiocarbamate Triethylammonium Salt and Tris(2-Chloroethyl) Phosphate A one-quarter portion of the product of Example 1 (0.25 mole, 249.3 grams), 900 milliliters acetone, and 23.8 grams of tris-(2-chloroethyl) phosphate (0.0833 mole) were mixed together in an Erlenmeyer flask. The reactants were stirred at ambient temperature over a course of 68 hours. The resulting precipitants were filtered off and the organic filtrate was concentrated on a rotary evaporator by removing all the volatiles. The yellowish, concentrated liquid was further filtered through a Buchner funnel to obtain 135.2 grams viscous liquid as the desired product.

Example 4

Reaction Product of Sodium N,N-Di-2-Ethylhexyl Dithiocarbamate and Tris(2-Chloroethyl) Phosphate A one-quarter portion of the above product of Example 2 (0.5 mole equivalent sodium N,N-di-2-ethylhexyl dithiocarbamate in toluene, 302 grams), 400 milliliters acetone, and 45.1 grams of tris-(2-chloroethyl) phosphate (0.158 mole) were mixed together in a one liter Erlenmeyer flask. The reactants were vigorously stirred at ambient temperature over a 24-hour period. The resulting sodium chloride precipitants were filtered off. Then the volatiles were removed from the organic solution by distillation at reduced pressure to produce about 197 grams of a viscous, yellowish fluid. It was further purified by hot filtration through Super-Gel.

| | |
|---|---|
| Nitrogen analysis | 3.1% (theory 3.7%) |
| Sulfur analysis | 13.9% (theory 17.0%) |
| Phosphorus analysis | 2.2% (theory 2.7%) |

Example 5

Reaction Product of Sodium N,N-Di-Ethyl Dithiocarbamate and Tris(2-Chloroethyl) Phosphate 113 grams of sodium N,N-di-ethyl dithiocarbamate trihydrate (obtained commercially, 0.5 mole), 600 milliliters of acetone, and 47.6 grams of tris(2-chloroethyl) phosphate (0.166 mole) were mixed together with strong agitation for 24 hours at ambient temperature. After the filtration and similar work-up procedure as described in Examples 3 and 4, a light yellowish material was obtained (126.6 grams).

Products of the examples were blended into synthetic lubricating oils and evaluated for antioxidant performance by Catalytic Oxidation Test at 325° F. for 40 hours (Table 1); Catalytic Oxidation Test at 375° F. for 24 hours (Table 2).

Catalytic Oxidation Test

Basically, the test lubricant is subjected to a stream of air which is bubbled through at the rate of five liters per hour respectively at 325° F. for 40 hours or at 375° F. for 24 hours. Present in the composition are samples of metals commonly used in engine construction, namely, iron, copper, aluminum, and lead. See U.S. Pat. No. 3,682,980, incorporated herein by reference, for further details of the test.

TABLE 1

| Catalytic Oxidation Test 40 Hours at 325° F. | | | |
|---|---|---|---|
| Item | Additive Conc. (wt %) | Percent Change in Viscosity $\Delta KV$, % | Change in Acid Number $\Delta TAN$ |
| Base Oil (ISO VG 680 Synthetic Oils) | — | 292.6 | 8.05 |
| Example 3 in above base oil | 1.0 | 1.9 | −0.22 |
| Example 4 in above base oil | 1.0 | 6.0 | 0.49 |
| 4,4'-methylene bis(2,6-di-tert-butylphenol) | 1.0 | 10.6 | 1.89 |

TABLE 2

| Catalytic Oxidation Test 24 Hours at 375° F. | | | |
|---|---|---|---|
| Item | Additive Conc. (wt %) | Percent Change in Viscosity $\Delta KV$, % | Change in Acid Number $\Delta TAN$ |
| Base Oil (ISO VG 680 Synthetic Oils) | — | 1201.4 | 5.70 |
| Example 3 in above base oil | 1.0 | 27.4 | 3.39 |
| Example 4 in above base oil | 1.0 | 32.8 | 4.07 |
| 4,4'-methylene bis(2,6-di-tert-butylphenol) | 1.0 | 79.3 | 4.34 |

As shown above, the products of this invention show very good antioxidant activity as evidenced by control of increase in acidity and viscosity, and even outperform the traditional hindered phenol antioxidant.

The dithiocarbamate-drived phosphates were also evaluated for antiwear performance using the Four-Ball Wear Test (Tables 3 and 4).

Four-Ball Wear Test

Three stationary balls are placed in a lubricant cup and the lubricant containing the compound to be tested is added thereto, and a fourth ball is placed in a chuck mounted on a device which can be used to spin the ball at known speeds and loads. The samples were tested using ½ inch stainless steel balls of 52100 steel for 30 minutes.

TABLE 3

| | Four-Ball Test | | | |
|---|---|---|---|---|
| | Wear Scar Diameter in mm, 30 Minute Test 60 kg Load | | | |
| Item | 1000 rpm 200° F. | 200 rpm 200° F. | 1000 rpm 300° F. | 2000 rpm 300° F. |
| Base Oil (80% Solvent Paraffinic Bright 20% Solvent Paraffinic Neutral Mineral Oils) | 1.89 | 2.44 | 1.84 | 2.45 |
| 1% Example 3 in above base oil | 0.64 | 0.66 | 0.63 | 0.66 |
| 1% Example 4 in above base oil | — | — | — | 1.66 |

TABLE 4

| | Four-Ball Test |
|---|---|
| Item | Wear Scar Diameter in mm 20 kg Load, 60 Minute, 1800 rpm and 130° F. |
| Base Oil (80% Solvent Paraffinic Bright, 20% Solvent Paraffinic Neutral Mineral Oils) | 0.84 |
| 1% Example 3 in above base oil | 0.54 |

As can be seen from the above wear test results, the products described exhibit considerable antiwear activity.

These dithiocarbamate-derived phosphate products also were subjected to standard corrosion test (ASTM-D130-80). The results shown to Table 5 below showed no deleterious effect on corrosivity to the base oil.

TABLE 5

| Copper Strip Corrosivity Test (3 Hours, 250° F.) | | |
|---|---|---|
| Item | Additive Conc. (wt %) | Corrosivity Rating |
| Base Oil (ISO VG 680 Synthetic Oil) | — | 1 b |
| Example 3 in above base oil | 1.0 | 1 b |
| Example 4 in above base oil | 1.0 | 1 b |

The data disclosed in the Tables hereinafter confirm that the novel compositions described herein are useful at low concentration as well as possessing multifunctional activity. Such compositions significantly enhance the stability, reduce wear and extend service life.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

We claim:

1. A N,N-dihydrocarbyl dithiocarbamate-derived organic phosphate product of reaction prepared as in the following generalized equation:

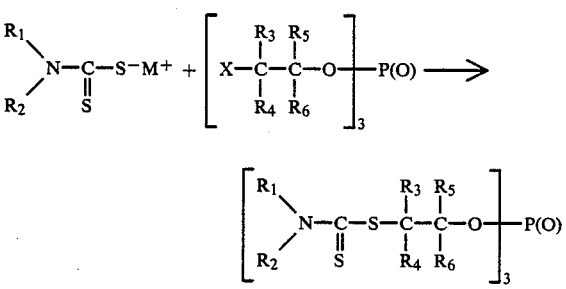

where $R_1$ and $R_2$ are each individually hydrogen or $C_1$ to about $C_{60}$ hydrocarbyl, $R_3$, $R_4$, $R_5$ and $R_6$ are each individually hydrogen or $C_1$ to about $C_{30}$ hydrocarbyl and each of said $R_1$, $R_2$, $R_3$, $R_4$, $R_5$ and $R_6$ can optionally contain sulfur, nitrogen and/or oxygen; $M^+$ represents the cationic moiety of the dithiocarbamate salt and X is halide selected from chloride, bromide or iodide.

2. The product of claim 1 where $M^+$ is selected from the group consisting of alkali metal ions, trihydrocarbyl/trialkylammonium ions and calcium ions, $Ca^{2+}$, or mixtures thereof.

3. The product of claim 2 wherein the alkali metal ions are selected from $Na^+$, $K^+$ or $Li^+$, and $R_7$ is selected from ethyl, methyl, propyl and butyl or mixtures thereof.

4. The product of claim 3 wherein the alkali metal ion is $Na^+$.

5. The product of claim 4 wherein $R_7$ is ethyl.

6. The product of claim 2 where the trihydrocarbyl/trialkylammonium ion has the following generalized formula:

$$(R_7)_3N^+H$$

where $R_7$ is $C_1$ to about $C_{60}$ alkyl and can optionally contain sulfur, nitrogen and/or oxygen.

7. The product of claim 1 wherein the dithiocarbamate salt is sodium N,N-di-2-ethylhexyl dithiocarbamate.

8. The product of claim 1 wherein the dithiocarbamate salt is the triethylammonium salt of N,N-dicoco dithiocarbamate.

9. The product of reaction of claim 1 wherein the product is derived from N,N-dicoco dithiocarbamate triethylammonium salt and tris(2-chloroethyl) phosphate.

10. The product of reaction of claim 1 wherein the product is derived from sodium N,N-di-2-ethylhexyl dithiocarbamate and tris(2-chloroethyl) phosphate.

11. The product of reaction of claim 1 wherein the product is derived from sodium N,N-diethyl dithiocarbamate and tris(2 chloroethyl) phosphate.

12. The product of claim 1 wherein the reaction takes place in the presence of a hydrocarbon solvent.

13. The product of claim 12 wherein the solvent is toluene.

14. A lubricant composition comprising a major amount of an oil of lubricating viscosity or grease prepared therefrom and a minor amount of a product of reaction prepared as in the following generalized equation:

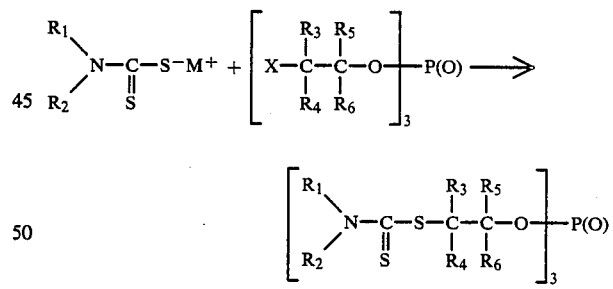

where $R_1$ and $R_2$ are each individually hydrogen or $C_1$ to about $C_{60}$ hydrocarbyl, $R_3$, $R_4$, $R_5$ and $R_6$ are each individually hydrogen or $C_1$ to about $C_{30}$ hydrocarbyl and each of said $R_1$, $R_2$, $R_3$, $R_4$, $R_5$ and $R_6$ can optionally contain sulfur, nitrogen and/or oxygen; $M^+$ represents the cationic moiety of the dithiocarbamate salt and X is halide selected from chloride, bromide or iodide.

15. The lubricant composition of claim 14 wherein $M^+$ is selected from the group consisting of alkali metal ions, $(R_7)_3N^+H$, calcium ions, and where $R_7$ is $C_1$ to about $C_{60}$ alkyl or $C_1$ to about $C_{12}$ hydrocarbyl.

16. The lubricant composition of claim 14 wherein X is chloride and $R_3$, $R_4$, $R_5$ and $R_6$ are each hydrogen.

17. The lubricant composition of claim 16 wherein the alkali metal ions are selected from $Na^+$, $K^+$ or $Li^+$ and $R_7'$ is selected from methyl, ethyl, propyl and butyl or mixtures thereof.

18. The lubricant composition of claim 17 wherein $R_7$ is ethyl.

19. The lubricant composition of claim 15 wherein $M^+$ is $Na^+$.

20. The lubricant composition of claim 14 wherein the dithiocarbamate salt is sodium N,N-di-2-ethylhexyl dithiocarbamate.

21. The lubricant composition of claim 14 wherein the dithiocarbamate salt is the triethylammonium salt of N,N-dicoco dithiocarbamate.

22. The lubricant composition of claim 14 wherein the product is derived from N,N-dicoco dithiocarbamate triethylammonium salt and tris(2-chloroethyl) phosphate.

23. The lubricant composition of claim 14 wherein the product is derived from sodium N,N-di-diethylhexyl dithiocarbamate and tris(2-chloroethyl) phosphate.

24. The lubricant composition of claim 14 wherein the product is derived from sodium N,N-diethyl dithiocarbamate and tris(2-chloroethyl)phosphate.

25. The lubricant composition of claim 14 wherein said oil of lubricating viscosity is selected from mineral oils, synthetic oils and mixtures of mineral and synthetic oils.

26. The lubricant composition of claim 25 wherein said oil of lubricating viscosity is a mineral oil.

27. The lubricant composition of claim 25 wherein said oil of lubricating viscosity is a synthetic oil.

28. The product of claim 14 wherein said product is derived from the reaction of N,N-dicocodithiocarbamate triethylammonium salt and tris(2-chloroethyl) phosphate.

29. The lubricant composition of claim 14 wherein said lubricating comprises a grease prepared from said mineral oils, synthetic oils or mixture of such oils of lubricant viscosity.

30. An additive product of reaction of improved antioxidant/antiwear characteristics having the following general structure:

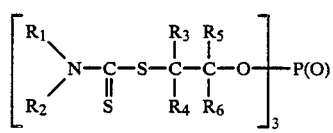

31. The product of claim 30 wherein said product is derived from sodium N,N-diethylhexyl dithiocarbamate and tris(2-chloroethyl) phosphate.

32. The product of claim 30 wherein said product is derived from sodium N,N-diethyl dithiocarbamate and tris(2-chloroethyl) phosphate.

33. The product of claim 32 where X is chloride and $R_3$, $R_4$, $R_5$ and $R_6$ are each hydrogen.

* * * * *

UNITED STATES PATENT AND TRADEMARK OFFICE
CERTIFICATE OF CORRECTION

PATENT NO. : 4,919,830

DATED : April 24, 1990

INVENTOR(S) : L. O. Farng et al

It is certified that error appears in the above-identified patent and that said Letters Patent is hereby corrected as shown below:

| Col. | Line # | |
|---|---|---|
| 2 | 62 | Change $[(R_1)_3 N^+ H]$ to $[(R_7)_3 N^+ H]$ |

Signed and Sealed this

Seventeenth Day of September, 1991

Attest:

HARRY F. MANBECK, JR.

Attesting Officer     Commissioner of Patents and Trademarks